United States Patent
Patel et al.

(10) Patent No.: US 6,906,018 B1
(45) Date of Patent: *Jun. 14, 2005

(54) EXTRUDABLE SOAP BARS COMPRISING HIGH LEVELS OF SUGARS

(75) Inventors: Rajesh Patel, Lyndhurst, NJ (US); Yury Yarovoy, Berkeley Heights, NJ (US); Charles Craig Nunn, Rutherford, NJ (US); Joseph Oreste Carnali, Pompton Plains, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/920,538

(22) Filed: Aug. 18, 2004

(51) Int. Cl.$^7$ .................................................. A61K 7/50
(52) U.S. Cl. ....................... 510/141; 152/153; 152/155; 152/156; 152/481; 152/484
(58) Field of Search ................................. 510/141, 144, 510/147, 151, 152, 153, 155

(56) References Cited

U.S. PATENT DOCUMENTS 5,194,172 A * 3/1993 Taneri et al. ................ 510/145

* cited by examiner

*Primary Examiner*—Necholus Ogden
(74) *Attorney, Agent, or Firm*—Ronald A. Koatz

(57) ABSTRACT

The invention provides bar compositions with high level of sugar or sugars (greater than about 25% by wt.) and which can be extruded.

8 Claims, No Drawings

EXTRUDABLE SOAP BARS COMPRISING HIGH LEVELS OF SUGARS

FIELD OF THE INVENTION

The present invention relates to bars comprising high levels of sugar or sugars (greater than about 25% by wt.) which may surprisingly be prepared by an extrusion process rather than a cast melt process. Specifically, by using co-structurants and processing in a specific way, bars of acceptable yield stress (e.g., 90 to 300 kilopascals) are obtained.

BACKGROUND OF THE INVENTION

Bars comprising relatively small amounts of surfactant (e.g., less than about 25% by wt.) and high amounts of sugar (greater than about 40% by wt.) have been disclosed, for example, in applicants' co-pending application entitled "Skin Cleansing Bar Comprising High Levels of Saccharides", U.S. Ser. No. 10/682,698 to Patel et al., filed Oct. 9, 2003, hereby incorporated by reference into the subject application ('698). Compositions of the '698 application also comprises 5 to 20% by wt. glass transition modifier and 1 to 30% by wt. water.

While the compositions of '698 comprise large amounts of sugar, the level of soap (e.g., fatty acid soap) is never required to be at least 20%, preferably at least 30% of the composition, nor is there an appreciation that special processing steps must be conducted to ensure that such high levels of soap and sugar can be extruded.

Unexpectedly, applicants have found that, by requiring floor level amounts of soap (i.e., at least 20%, preferably at least 30% by wt. of soap) and by ensuring certain process criticalities are met, it is possible to produce the bar compositions through an extrusion route (e.g., after mixing, optionally milling, cooling and optionally stamping) rather then, as previous believed, only producing such bars through a melt cast route. Bars made following both the composition and process criticalities of the invention will have optimal yield stress (e.g., 90 to 300 kilopascal (kPa), wherein yield stress is measured by equation 122.6/length of cut (in centimeters) made in a bar cut by cheesewire, as defined in protocol section) such that they can be readily extrudable, high sugar bars.

In a second embodiment of the invention, the invention comprises a process for making a low surfactant, high sugar bar (the less surfactant and the more sugar used provides good economic advantage in bar manufacture) via an extrusion route which process comprises mixing at least 20%, preferably at least 25%, more preferably at least 30% soap with sufficient water (i.e., 15–25% $H_2O$) and at sufficient temperature (above about 50° C.) to ensure soap solubility; and only subsequently mixing in sugars (optimally adding those with more reducing groups subsequent to those with fewer or none). Co-structurants can be added either with the soap and water, or with the sugar(s). Water levels are adjusted to ensure optimal yield stress after all ingredients are mixed and prior to milling (optional step), chilling and extrusion.

The '698 application noted above contemplates production only by melt cast route. Other art of which applicants are aware also either does not contemplate production of high sugar bars by extrusion route or does not use high sugar and high fatty acid soap criticalities (let alone envisage the process criticalities required when both are used) as required in the subject invention.

U.S. Pat. No. 6,376,441 to Ross et al. discloses a multi-phase melt cast bar.

U.S. Pat. No. 6,475,979 discloses bar which may have 5–90% surfactant and 10–85% which can be carbohydrate structurant such as starch or maltodextrin. The invention contemplates use of a reduced maltosaccharide which does not discolor during processing. There is no disclosure, however, of the high sugar, high fatty acid requirements of the invention; no disclosure that soap synthetic be less than about 52%, preferably less than 50%, more preferably less than about 45% by wt. composition; and no disclosure of the processing requirements needed when extruding such compositions.

U.S. Pat. No. 5,756,438 discloses a cleansing bar containing 40% to 80% of filler such as dextrin/dextrose to reduce cost is to 45% non-soap detergent and 0.10 to 20% waxy binder. These are non-soap detergents.

U.S. Pat. No. 6,680,285 to Abbas et al. discloses skin cleansing bar with 15–60% by wt. surfactant and 5 to 20% emollient. Again, the high soap, low surfactant and the process criticalities of the present invention are not contemplated.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term comprising is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

BRIEF DESCRIPTION OF THE INVENTION

In one embodiment, the present invention relates to extrudable bar compositions comprising:

(1) at least about 20% by wt., preferably at least 25%, more preferably about 30%, more preferably about 35% and even more preferably about 40% to 52% fatty acid soap;

(2) 0 to 30% by wt., preferably 1 to 20% surfactant other than soap (preferably anionic synthetic surfactant) such that total of (1) and (2) is less than 55% by wt. bar composition preferably less than 50%, more preferably less than 45% and even more preferably less than about 40% by wt.;

(3) greater than about 25%, preferably greater than about 30% to about 50% by wt. sugar or combination of sugars;

(4) about 0.5 to 10% by wt., preferably about 1 to 8% of a co-structurant (e.g., salt; or inorganic or organic filler); and (5) about 4 to 12%, preferably 6 to 10% water; of final bar water, wherein bar is made by process described below;

wherein final water level is adjusted to provide bar with yield about 90 to 300 kilopascal (kPa).

In a second embodiment of the invention, the invention comprises a process for making bars as noted above by an extrusion process wherein said process comprises:

(1) first mixing at least 20%, preferably at least about 30%, more preferably at least about 35%, even more preferably about 40% to about 50% soap with about 15 to 25% water at temperature of about 50° C. until substantially homogeneous;

(2) subsequently adding greater than about 25% by wt. sugar or sugars;

(3) adding co-structurant (about 0.5 tol 0% by wt.), minors and optional synthetic surfactants during steps 1 or 2;

(4) adjusting water level (e.g., by adding or eliminating water) to provide bar which extrudes and had yield stress of 90 to 300 kPa.

DETAILED DESCRIPTION OF THE INVENTION

In one embodiment, the present invention relates to bars having high levels of sugars, yet which can be extruded and stamped. The key to obtaining bars hard enough to extrude is the use of floor levels of fatty acid soap, maximum levels of total soap and synthetic surfactant and specific process conditions ensuring that soap and water are soluble prior to sugar addition. In a second embodiment, the invention provides specific conditions (e.g., order of addition, temperature) which must be met to ensure that extruded bars of correct yield stress are provided.

More specifically, in one embodiment, the invention provides novel, extrudable (e.g., with yield stress of 90 to 300 kPa bars comprising:

(1) at least about 20% to about 52%, preferably 35% to 50% by wt. fatty acid soap or blend of fatty acid soaps;

(2) 0 to 30%, preferably 1 to 20% by wt. surfactant other than soap such that (1) and (2) is less than 55% by wt., preferably less than 50% by wt. of bar composition;

(3) greater than about 25%, preferably greater than about 30% to about 50% by wt. sugar or sugars;

(4) about 0.5 to 10% by wt., preferably 1 to 8% by wt. of a co-structurant; and (5) about 4 to 12%, preferably 6 to 10% by wt. of the final bar water;

wherein said bars has yield stress of 90 to 300 kPa;

wherein said bars are made as described in the second embodiment of the invention.

In a second embodiment, there is disclosed a process for making such bars, and, as noted, this is discussed in greater detail below.

The composition of the invention are discussed in more detail below.

Soap

The compositions of the invention comprise at least about 20% by wt. to about 52% by wt. fatty acid soap. These are salts of $C_8$ to $C_{22}$ fatty acid salts. The fatty acids may be natural or synthetic aliphatic (alkanoic or alkenoic) acid salts.

Soaps having the fatty acid distribution of coconut oil may provide the lower end of the broad molecular weight range and are generally referred to as "soluble" fatty acid soaps, as defined above. Those soaps having the fatty acid distribution of peanut, tallow or rapeseed oil, or their hydrogenated derivatives (e.g. $C_{16}$ and higher), may provide the upper end of the molecular weight range and are generally referenced to as insoluble fatty acid soap.

In general soap making, it is preferred to use soaps having the fatty acid distribution of coconut oil or tallow, or mixtures thereof, since these are among the more readily available fats. The proportion of fatty acids having at least 12 carbon atoms in coconut oil soap is about 85%. The proportion will be greater when mixtures of coconut oil and fats such as tallow, palm oil, or non-tropical nut oils or fats are used, wherein the principal chain lengths are $C_{16}$ and higher. Soap stock with about 85% principally $C_{16}$–$C_{18}$ fatty acids (e.g., may have nominal amounts $C_{20}$ and higher) and about 15% principally $C_{12}C_{14}$ fatty acids (e.g., may have nominal amounts C10 or lower) is known as "85/15"; soap stock with about 65% principally $C_{16}$–$C_{18}$ fatty acids and about 35% principally $C_{12}$–$C_{14}$ fatty acids is known as "65/35" soap etc.

The soaps may contain unsaturation in accordance with commercially acceptable standards. Excessive unsaturation is normally avoided.

Salt counterions to the fatty acid may be those selected from alkali, ammonium or alkanolammonium ions. The term alkanolammonium refers to one, two or three $C_1$–$C_4$ hydroxyalkyl groups substituted onto a nitrogen cation, the triethanolammonium cation being the species of choice. Suitable alkali metal cations are those of potassium and sodium, the latter being preferred.

It is believed that fatty acid soaps interact with sugar and water to form gel like structures that provide bar hardness and cohesiveness.

Surfactant

While bars of the invention must comprise fatty acid soaps, they preferably also comprise balance of surfactant system (up to total soap and surfactant of less than 55%, preferably less than 50% by wt.) of a synthetic surfactant or surfactants. These may include surfactants selected from the group consisting of anionic surfactants, cationic surfactants, amphoteric surfactants, nonionic surfactants and mixtures thereof. Use of at least one anionic surfactant is preferred.

Anionic Surfactants

Anionic surfactants include, but are certainly not limited to aliphatic sulphate, aliphatic sufonate (e.g., $C_8$ to $C_{22}$ sulfonate or disulfonate), aromatic sulfonate (e.g., alkyl benzene sulfonate), alkyl sulfosuccinates, alkyl and acyl taurates, alkyl and acyl sarcosinates, sulfoacetates, alkyl phosphates, carboxylates, isethionates, etc.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

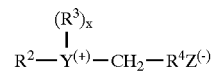

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

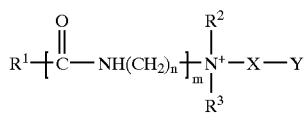

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is $-CO_2-$ or $-SO_3-$ Nonionic Surfactants The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_{6-22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Sugars

The commonly occurring crystallizable sugars belong to the class of mono- and disaccharides (Food Theory and Applications, edited by Pauline C. Paul and Helen H. Palmer, Wiley, New York, 1972, ISBN 0-471-67250-5). The class of monosaccharides includes dextrose, fructose, and galactose. The class of disaccharides includes sucrose, the most commonly used sweetener in the confectionery industry and the ingredient usually implied when the term "sugar" is used. Sucrose is a disaccharide composed of glucose and fructose residues joined by an α,β-glycosidic bond. Other common disaccharides include lactose, maltose, palatinose, and leucrose.

Sugars may also include oligosaccharides, which typically have 3 to 9 monosaccharide units, such as, for example, maltodextrin. Levels of such slightly more complex (although still fairly easily broken down) oligosaccharides are typically 0 to 7% by wt., preferably 1 to 5% by wt.

The sugars comprise greater than about 25% by wt., preferably greater than about 30% to about 60% by wt., preferably to about 50% of the composition. If maltodextrin (or other oligosaccharides of 3 to 9 monosaccharide units) is counted as a co-structurant, rather than as a sugar (which are mono- and disaccharides) then sugar levels are greater than below 25% by wt. to about 50%, preferably about 30% to about 45% by wt.

Co-Structurant

The bar compositions of the invention further comprise about 0.5 to about 10%, preferably 1 to 8% by wt. of a co-structurant salt; or inorganic or organic filler. Typically, the co-structurant will be water soluble. By water soluble is meant that it will have at least 1% solubility in water at room temperature (about 20° C.).

Among components which may be used are salts formed from, for example, reaction of group 2 and group 7 elements (e.g., calcium chloride); or any other salt (e.g., substance formed from anion of an acid and cation of a base).

In addition to salts, the co-structurant can be any solid filler component found in bar compositions as a replacement for soap or surfactant. One example is the solid alkylene glycols (e.g., polyethylene glycols). Examples of inorganic fillers include inorganic particulates such as talc, clays, zeolites, calcites, silicas, silicate (e.g., aluminum silicates such as feldspar mineral), carbonates (e.g., calcium magnesium carbonates such as dolomites), bicarbonates, borates, sulphates, etc. Examples of organic fillers include starches, proteins, waxes, etc.

The compositions of the invention also comprise about 4 to 12%, preferably 6 to 10% by wt. water in the final bar. As discussed below, this should not be confused with the fact that critical amounts of water are needed in processing (e.g., to solubilize soap) prior to addition of sugar or sugars.

Specifically, water is adjusted in the final stage of processing to ensure proper hardness of bars for extrudability. Bar compositions as defined above have yield stress of 90 to 300 kPa after water adjustment.

In a second aspect of the invention, the bars of the invention, as noted above, are made as follows.

(1) at least 20 to 50% soap is mixed with about 15 to 24% by wt. water at a temperature of at least about 50° C. until homogeneous; typically mixing is done using, for example a Z-blade mixer;

(2) subsequently, greater than about 25% by wt. sugar is added and mixed until homogeneous.

Preferably, to the extent there are mixtures of different types of sugar as well as sugars of different lengths (e.g., one unit monosaccharide sugars such as sucrose; disaccharides such as dextrose; or 9–13 unit oligomer sugars such as maltodextrose), the less reducing sugars (sugars less subject to oxidation), with fewer available hydroxyl groups (e.g., dextrose), are added first; and the more reducing sugars, with more available hydroxyl groups (e.g., maltodextrin), are added after reducing temperature (below 50° C.). This helps reduce browning which may occur when maltodextrin is used as a sugar.

The co-structurant/filler compound can be added either with the soap and water, or later when sugar or sugars are added. In preferred embodiments, they are added after the sugar.

The surfactant other than soap, if any, can also be added at either point.

After all minors and other compounds are mixed, the water level is adjusted (resulting in final level of water of up to 12% by wt.). The goal is to produce bars which will have yield stress of 90 to 300 kPa, preferably 100 to 200 kPa.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight. Further, all ranges are to be understood to encompass both the ends of the ranges plus all numbers subsumed within the ranges.

Protocol

Cheesewire

Yield stress is measured using a cheesewire apparatus. A 200.00 g weight is used and the cut is made by apparatus is measured in centimeter (cm) and the following calculation is used to measure yield stress:

$$\text{Yield stress}(kPa)=122.6/\text{Length of cut}(cm)$$

Procedure For Lather Generation From Bars:
1. Turn the bar 20 times in water at 90° F. Keep the bar aside for 10 minutes;
2. Turn the bar 10 times in water at 90° F.;
3. Take the bar out of water and shake both hands (plus bar) three times gently to discard excess water. This procedure more or less ensures that a constant quantity of water is used for lather generation;
4. Hold the bar with one hand and rub it on the palm of the other 10 times;
5. Put the bar down, collect all the lather in the center of the palm;
6. Rub this lather gently a further 10 times.

Procedure For Determining Wear Rate (Rate of Wear or ROW)
1. Take initial weight on soap bar;
2. Fill washing bowl with 5 liters of water at desired temperature (40° C.);
3. Wearing waterproof gloves immerse soap bar in water, remove from water and twist 15 times in the hand above water;
4. Repeat step 3;
5. Immerse soap bar in water to wash off lather and place soap bar in a tray;
6. Carry out the full wash procedure (Steps 1–5) six times per day for 4 consecutive days, at evenly spaced intervals during each day (e.g., 9:00, 10:00, 11:00, 12:00, 13:00, 14:00).

Calculate rate of wear=(initial weight−final weight).

Definitions

SCI=sodium cocoyl isethionate (anionic surfactant)
SDS=sodium dodecyl sulfate (anionic surfactant)
PVP=polyvinyl pyrollidone
PVA=polyvinyl acrylate
PEG=polyethylene glycol
HEC Methical 40–100=hydroxy methyl cellulose
SDS=sodium dodecyl sulphate
MD=maltodextrin
PAS=primary alkyl sulfate
YS=yield stress

TABLE 1

Examples bars prepared.

| Ingredients | Example 1 | Example 2* | Example 3* | Example 4 | Example 5 | Example 6 | Example 7* | Example 8 | Example 9 | Example 10 | Example 11 | Example 12 | Example 13 |
|---|---|---|---|---|---|---|---|---|---|---|---|---|---|
| Sugar | | | | | | | | | | | | | |
| Sucrose (sugar) | 40.0% | 50.0% | 50.0% | 50.0% | 50.0% | 50.0% | 50.0% | 30.0% | 30.0% | 40.0% | 40.0% | 40.0% | 40.0% |
| Surfactant | | | | | | | | | | | | | |
| 65/35 Soap blend (soap) | | | | | | | | 50.0% | | 40.0% | | 33.16% | 33.16% |
| 85/15 Soap blend (soap) | 22.0% | 23.0% | 20% | 23% | 22% | 22% | 25% | | 50.0% | | 40.0% | | |
| SCI (co-surfactant) | | 7.0% | | | | | | | | | | | |
| SDS (co-surfactant) | | | 5.0% | | | | | 2.0% | 2.0% | 2.0% | 2.0% | | |
| Water Soluble Polymer | | | | | | | | | | | | | |
| Maltodextrin (co-structurant) | 20.% | 10.0% | 10.0% | 5% | 10% | 5% | 10% | 5.0% | 5.0% | 5.0% | 5.0% | 5.0% | 5.0% |
| PVP (40K) (co-structurant) | | | | 5.0% | | | | | | | | | |
| PVA (co-structurant) | | | | | 4.0% | | | | | | | | |
| HEC Methocel 40–100 (co-structurant) | | | | | | 3.0% | | | | | | | |
| CaCl2 (co-structurant) | | | | | | | | 2.0% | 2.0% | | | | |
| PEG 8K (co-structurant) | | | | | | | | 0 | 0 | 5.0% | 5.0% | | |
| PEG Tallow (co-structurant) | | | | | | | | 0 | 0 | | | 10.0% | 10.0% |
| Water/perfume/minor | 12.5% | 14.0% | 8.4% | 8.2% | 5.0% | 5.0% | 8.0% | 11.0% | 11.0% | 8.0% | 8.0% | 11.84% | 11.84% |

*prepared using hydrated soap

TABLE 2

| Example | Formulation | RoW | Lather | Process |
|---|---|---|---|---|
| Comparative A | 60–80% Pure soap composition | 1.4 | 57 | Extrusion |
| Comparative B | Composition of invention w/low soap, high sugar and maltodextrin co-structurant, but made by cast melt route | 2.6 | 115 | Melt cast |
| Comparative C | Composition of invention w/low soap, high sugar and PVP co-structurant, but made by cast melt route | 3.1 | 105 | Melt cast |
| Comparative D | Extruded bar with 5% SDS and no co-structurant used | 4.7 | 55 | Extrusion |
| Comparative E | Extruded bar with SCI and no co-structurant used | 2.9 | 50 | Extrusion |
| Example 9 | 85/15 + 2% CaCl + Sugar/MD | 1.23 |  | Extrusion |
| Example 8 | 65/35 + 2% CaCl + Sugar/MD | 1.76 | 87.5 | Extrusion |
| Example 11 | 85/15 + 5% PEG8K + Sugar/MD | 1.79 |  | Extrusion |
| Example 10 | 65/35 + 5% PEG8K + Sugar/MD | 1.49 | 77.5 | Extrusion |
| Example 13 | 85/15 + 5% PEG Tallow + Sugar/MD | 1.1 |  | Extrusion |
| Example 12 | 65/35 + 5% PEG Tallow + Sugar/MD | 2.6 | 60.0 | Extrusion |

As seen from Examples 8–13 versus Comparatives, the rate of wear for bars of the invention was comparable to an extruded soap bar (Comparative A) and better than Comparative B, C, D and E.

EXAMPLE 14

Another advantage of extruded bars relative to cast melt bars of, for example, U.S. Ser. No. 10/682,698 is that they do not shrink during storage and show less tendency for discoloration (browning). This is seen in Table 3 below:

TABLE 3

Stability data after 30, 60 and 90 days

|  | Extruded bars | Melt cast bars |
|---|---|---|
| Shrinking | No | Strong |
| Browning | Minor | Strong |

| Ex. | 1 Soap Level | 2 Soap Type | 3 PAS Level | 4 N Soap Water (level add. At proces) | 5 N Soap Temp | 6 Water added at processing | 7 PEG 8000 Level | 8 MD Level (Maltodextrin) | Sucrose Level | Final Bar Water | Temp (extru) | YS (extru) | BLAM (init) | ROW (1 wk) | Crack (1 wk) |
|---|---|---|---|---|---|---|---|---|---|---|---|---|---|---|---|
| Comp. F | 60–80% | — | — | — | — | 13% | — | — | — | — | 40 | 491 | 65.00 | 1.37 | 3.5 |
| Comp. G | 60–80% | — | — | — | — | 13% | — | — | — | — | 40 | 491 | 55.00 | 1.40 | 1.5 |
| 15 | 50% | 65/35 | 10% | 16% | 70 | 4% | 10% | 5% | 22% | 4.5% | 50.0 | 368 |  | 2.60 | 0.0 |
| 16 | 40% | 65/35 | 2% | 16% | 70 | 10% | 10% | 0% | 35% | 9.1% | 42.0 | *61 |  | 2.30 | 0.0 |
| 17 | 40% | 85/15 | 2% | 24% | 100 | 10% | 5% | 0% | 40% | 9.1% | 49.0 | 123 |  | 1.58 | 0.0 |
| 18 | 40% | 65/35 | 10% | 24% | 100 | 4% | 10% | 0% | 33% | 4.4% | 45.0 | 210 |  | 2.28 | 0.0 |
| 19 | 40% | 85/15 | 10% | 16% | 70 | 4% | 5% | 0% | 38% | 4.9% | 45.0 | 294 |  | 1.14 | 0.0 |
| 20 | 50% | 85/15 | 2% | 16% | 70 | 10% | 5% | 5% | 25% | 7.6% | 56.0 | 147 |  | 0.80 | 0.0 |
| 21 | 50% | 65/35 | 2% | 24% | 100 | 10% | 10% | 5% | 20% | 8.0% | 40.0 | 134 |  | 0.17 | 0.0 |
| 22 | 50% | 85/15 | 10% | 24% | 100 | 4% | 5% | 5% | 23% | 4.9% | 50.0 | 368 |  | 2.30 | 3.5 |
| 23 | 50% | 85/15 | 2% | 24% | 70 | 4% | 10% | 0% | 31% | 3.8% | 45.0 | 210 | 45.00 | 1.30 | 0.0 |
| 24 | 50% | 85/15 | 10% | 16% | 100 | 10% | 10% | 0% | 17% | 11.0% | 40.0 | 78 | 67.50 | 2.30 | 4.0 |
| 25 | 40% | 65/35 | 10% | 16% | 100 | 10% | 5% | 5% | 27% | 10.0% | 40.0 | 82 | 62.50 | 1.90 | 3.5 |
| 26 | 40% | 85/15 | 10% | 24% | 70 | 10% | 10% | 5% | 22% | 11.2% | 40.0 | 39 | 57.50 | 2.50 | 0.0 |
| 27 | 50% | 65/35 | 2% | 16% | 100 | 4% | 5% | 0% | 36% | 3.4% | 50.0 | 368 | 60.00 | 1.90 | 0.0 |
| 28 | 50% | 65/35 | 10% | 24% | 70 | 10% | 5% | 0% | 22% | 10.7% | 45.0 | *87 | 72.50 | 2.40 | 0.0 |
| 29 | 40% | 85/15 | 2% | 16% | 100 | 4% | 10% | 5% | 36% | 3.0% | 50.0 | 294 | 40.00 | 1.10 | 0.0 |
| 30 | 40% | 65/35 | 2% | 24% | 70 | 4% | 5% | 5% | 41% | 3.3% | 50.0 | 491 | 62.50 | 2.20 | 0.0 |
| 31 | 40% | 65/35 | 2% | 24% | 50 | 4% | 10% | 0% | 41% | 3.9% | 46.0 | 210 |  | 2.60 | 0.0 |
| 32 | 50% | 65/35 | 2% | 16% | 50 | 6% | 5% | 0% | 34% | 6.1% | 54.0 | 210 |  | 1.90 | 0.0 |
| 33 | 50% | 65/35 | 2% | 16% | 50 | 6% | 5% | 0% | 34% | 6.2% | 40.0 | 245 | 62.50 | 2.40 | 0.0 |
| 34 | 40% | 65/35 | 2% | 24% | 70 | 4% | 5% | 5% | 41% | 4.3% | 54.0 | 113 |  | 2.26 | 0.0 |
| 35 | 40% | 65/35 | 10% | 24% | 100 | 4% | 10% | 5% | 28% | 5.1% | 50.0 | 245 |  | 2.09 | 0.0 |
| 36 | 40% | 65/35 | 6% | 24% | 70 | 6% | 10% | 5% | 30% | 6.3% | 55.0 | 245 |  | 2.16 | 0.0 |
| 37 | 40% | 65/35 | 6% | 24% | 70 | 6% | 10% | 5% | 30% | 6.0% | 45.0 | 105 |  | 2.00 | 0.0 |
| 38 | 40% | 65/35 | 2% | 24% | 70 | 6% | 10% | 5% | 34% | 6.8% | 45.0 | 134 |  | 1.84 | 0.0 |
| 39 | 40% | 65/35 | 10% | 24% | 70 | 6% | 10% | 5% | 26% | 6.1% | 45.0 | 147 |  |  |  |

From Examples 15–39, several things can be seen comparing to the Comparatives F & G.

Specifically, it can be seen that extruded bars have comparable foam (BLAM test), comparable rate of wear, and superior crack score (i.e., crack values of 0, signifying no crack problem at all.

The Example also show how processing levels of water are far higher than final numbers.

EXAMPLE 40

An example of formulation using lower amounts of soap (e.g., 21.16% by wt.) is set forth below:

| Component | Function | % By wt. |
|---|---|---|
| Sucrose | Filler | 50.00 |
| Sodium soap | Anionic surfactant | 21.16 |
| Maltodextrin (MD) | Filler | 10.00 |
| Water | | 10.00 |
| Sodium cocoyl isethionate | Anionic surfactant | 7.00 |
| Fragrance | Perfume | 1.00 |
| Titanium dioxide | Whitener | 0.80 |
| Preservatives | | 0.04 |

Sodium soap was prepared in a mixer by mixing 85/15 soap with 30% water at 100° C. in the mixer.

What is claimed is:

1. Extrudable bar composition comprising:
   (1) at least 20% by wt. fatty acid soaps;
   (2) 0 to 30% surfactant other than soap such that total of (1) and (2) is less than about 55% total;
   (3) greater than 25% by wt. reducing and/or non-reducing sugar or sugars;
   (4) 0.5 to 10% by wt. co-structurant which is a water soluble polymer;
   (5) 4 to 10% by wt final water content of bar, wherein said bar made as follows:
      (a) first mixing about 15–25% water and fatty acid soaps of (1) at temperature greater than about 50° Celsius to about 100° Celsius until substantially homogeneous;
      (b) subsequently adding sugar or sugars of (3);
      (c) adding co-structurant and minors each independently or both together, during step (a) or (b); and
      (d) adjusting water level prior to extruding such that final water level of (5) is obtained and yield stress of final bar is 90 to 300 kPa.

2. Bar according to claim 1, comprising at least 25 to 52% by wt. soap.

3. Bar according to claim 1 comprising 1 to 20% by wt. surfactant other than soap.

4. Bar according to claim 3, wherein total of (1) and (2) is less than 50% by wt.

5. Bar according to claim 1, wherein surfactant is anionic surfactant.

6. Bar according to claim 1, comprising 30% to about 60% by wt. sugar or combination of sugar.

7. Bar according to claim 1, comprising 1 to 8% by wt. co-structurant.

8. Bar according to claim 1, comprising 6 to 10% final water.

* * * * *